United States Patent [19]

Golik

[11] Patent Number: 4,837,206
[45] Date of Patent: Jun. 6, 1989

[54] ESPERAMICIN DERIVATIVES

[75] Inventor: Jerzy Golik, Southington, Conn.

[73] Assignee: Bristol-Myers Company, New York, N.Y.

[21] Appl. No.: 43,916

[22] Filed: Apr. 29, 1987

[51] Int. Cl.$^4$ ...................... A61K 31/70; C07H 15/04
[52] U.S. Cl. .................................. 514/25; 536/16.8;
536/17.2; 536/17.5; 536/17.6; 536/17.9;
536/18.1; 514/61
[58] Field of Search ..................... 536/16.8, 17.5, 17.6,
536/18.1, 17.9, 17.2; 514/25, 61

[56] References Cited

U.S. PATENT DOCUMENTS

| | | | |
|---|---|---|---|
| 4,530,835 | 6/1985 | Bunge et al. | 435/169 |
| 4,578,271 | 3/1986 | Kiyoto et al. | 435/128 |
| 4,661,353 | 4/1987 | Wilton et al. | 435/169 |
| 4,675,187 | 6/1987 | Konishi et al. | 435/170 |

OTHER PUBLICATIONS

J. Antibiotics, 38 (11), 1605–1609, 1985.
Cran et al., *Organic Chemistry*, 2nd Ed., 1969, p. 361.

*Primary Examiner*—Johnnie R. Brown
*Assistant Examiner*—Elli Peselev
*Attorney, Agent, or Firm*—David M. Morse

[57] ABSTRACT

Novel N-acetyl derivatives designated N-acetylesperamicins $A_1$, $A_2$ and $A_{1b}$ are prepared by acetylating known antitumor antibiotics. The new derivatives exhibit both antimicrobial and antitumor activity and have the structures

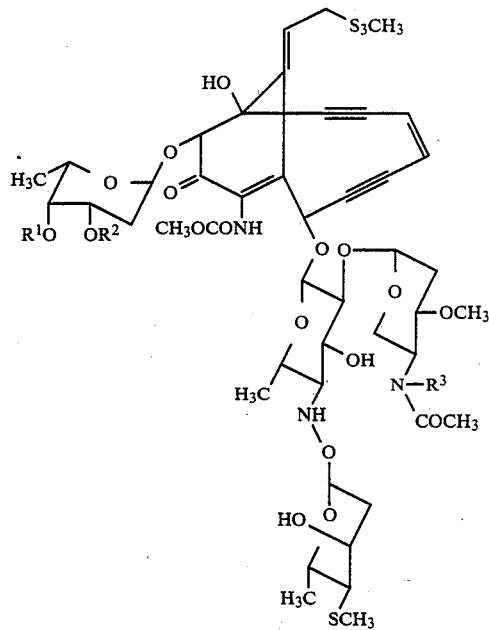

wherein $R^1$ and $R^2$ are hydrogen or

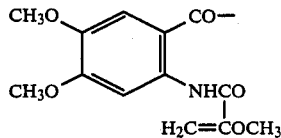

and $R^3$ is —CH(CH$_3$)$_2$ or —CH$_2$CH$_3$.

5 Claims, 4 Drawing Sheets

13C NMR SPECTRUM OF N-ACETYLESPERAMICIN A1
(90.6 MHz IN CDCl3)

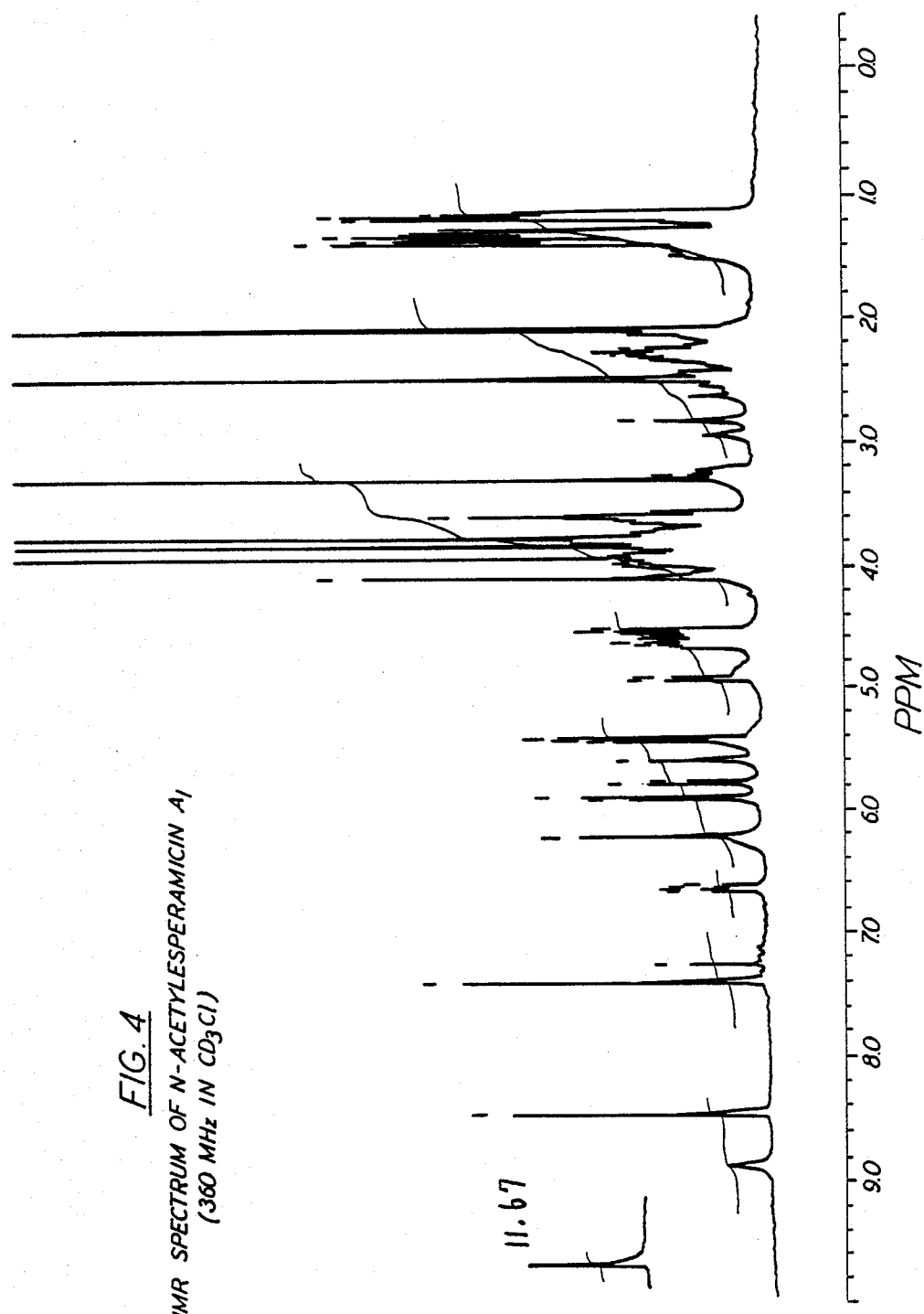

ESPERAMICIN DERIVATIVES

BACKGROUND OF THE INVENTION

1. Field of the Invention

This invention relates to new antitumor antibiotic substances and to their production and use.

2. Description of the Prior Art

U.K. Patent Application No. 2,141,425A discloses fermentation of certain strains of *Actinomadura verrucosospora* to produce an antitumor antibiotic complex designated BBM-1675 (later called esperamicin). This complex may be separated into two major bioactive components, BBM-1675 $A_1$ and $A_2$ (also called esperamicin $A_1$ and $A_2$) and four minor components designated BBM-1675 $A_3$, $A_4$, $B_1$ and $B_2$. Structures for the esperamicins were not provided in the U.K. reference.

U.S. patent application Ser. No. 770,335 filed Aug. 27, 1985 discloses antitumor antibiotic substances designated BBM-1675C and BBM-1675D produced by selective chemical hydrolysis of esperamicin $A_1$ and $A_2$.

U.S. Pat. No. 4,530,835 discloses fermentation of *Streptomyces* sp. ATCC 39363 to produce the antitumor antibiotics designated CL-1577A and B of unknown structure. Applicant believes that CL-1577A and B are identical to BBM-1675 $A_1$ and $A_2$.

U.S. Pat. No. 4,578,271 discloses fermentation of *Actinomadura pulveraceus* sp. nov. No. 6049, ATCC 39100, to produce the antitumor antibiotics WS 6049-A and -B of unknown structure. A culture of this organism has been deposited by applicant in the American Type Culture Collection, Rockville, Md., and added to its permanent collection of microorganisms as ATCC 53610.

Applicant's colleagues have isolated an antitumor antibiotic designated BBM-1675 $A_{1b}$ (esperamicin $A_{1b}$) from the *Actinomadura verrucosospora* strain H964-62, ATCC 39334, culture disclosed in U.K. Patent Application No. 2,141,425A which they believe is identical with WS 6049-A disclosed in U.S. Pat. No. 4,578,271 (see *J. Antibiotics* 38 (11), 1605–1609, 1985).

Subsequent to the publication of the above-described references, applicant and his colleagues have determined the structure of esperamicins $A_1$, $A_2$ and $A_{1b}$. These structures are indicated below.

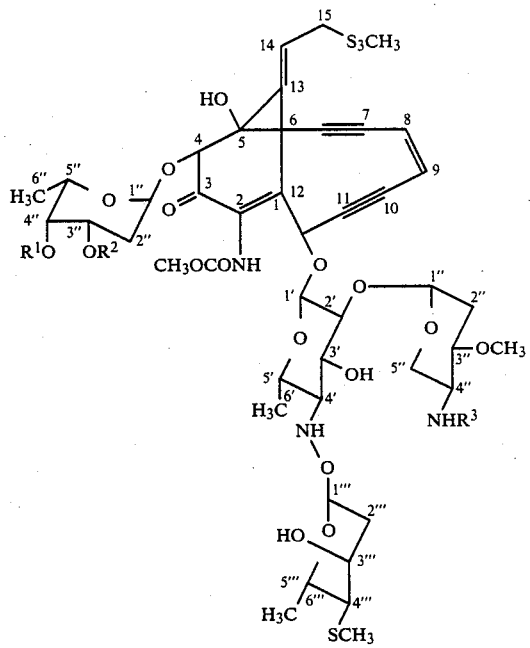

| Compound | $R^1$ | $R^2$ | $R^3$ |
|---|---|---|---|
| esperamicin $A_1$ | H | AC | $CH(CH_3)_2$ |
| esperamicin $A_2$ | AC | H | $CH(CH_3)_2$ |
| esperamicin $A_{1b}$ | H | AC | $CH_2CH_3$ |

AC =

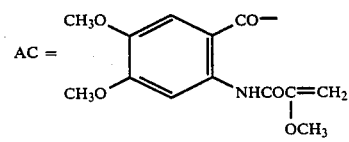

SUMMARY OF THE INVENTION

Applicant provides by the present invention novel synthetic derivatives of esperamicins $A_1$, $A_2$ and $A_{1b}$, as described above, which have the structures

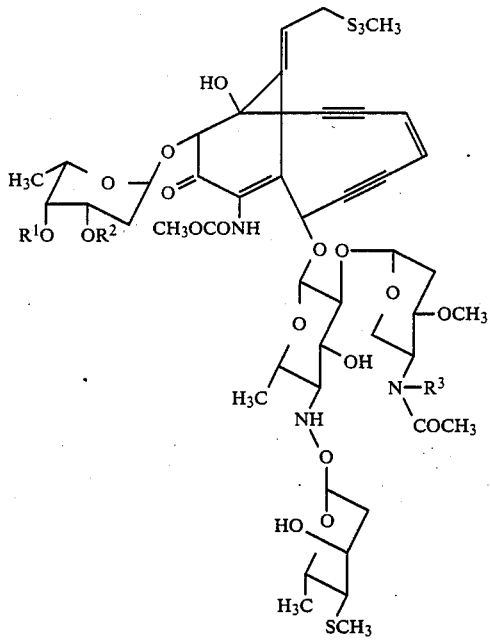

| Compound | R[1] | R[2] | R[3] |
|---|---|---|---|
| N—acetylesperamicin $A_1$ | H | AC | $CH(CH_3)_2$ |
| N—acetylesperamicin $A_2$ | AC | H | $CH(CH_3)_2$ |
| N—acetylesperamicin $A_{1b}$ | H | AC | $CH_2CH_3$ |

AC = 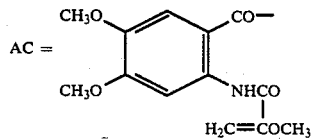

As can be seen the compounds of the present invention have an acetyl group replacing a hydrogen atom on the amino sugar moiety. These new synthetic derivatives have been found to possess potent antitumor activity in in vitro cytotoxicity tests and also in in vivo experimental animal systems. They also inhibit the growth of pathogenic bacteria.

The invention also provides a process for preparing the above-described N-acetyl derivatives, which process comprises reacting the appropriate esperamicin $A_1$, $A_2$ or $A_{1b}$ starting material in an inert organic solvent with a suitable acetylating reagent, e.g. acetic anhydride, and then recovering the desired N-acetyl product.

DESCRIPTION OF THE DRAWINGS

FIG. 4 shows the proton magnetic resonance spectrum of N-acetylesperamicin $A_1$ in $CD_3Cl$ (360 MHz).

DETAILED DESCRIPTION

The N-acetyl derivatives of the present invention may be prepared by methods known per se. Conveniently the derivatives are prepared by reacting the appropriate esperamicin starting material, i.e. esperamicin $A_1$, $A_2$ or $A_{1b}$, in an inert organic solvent, e.g. a halogenated hydrocarbon such as methylene chloride or chloroform, methanol, ethanol, etc., with an acetylating agent, preferably acetic anhydride. The reaction may be carried out over a wide temperature range, but room temperature conditions or slightly elevated temperatures (30° C.) are preferably employed. Best yields have been obtained when the reaction is stirred under an inert atmosphere, e.g. Argon, for a period of from about 16-48 hours. Progress of the reaction may be followed by thin layer chromatography.

The esperamicin $A_1$ and $A_2$ starting materials may be prepared as described in U.K. Patent Application No. 2,141,425A or in U.S. Pat. No. 4,530,835. Esperamicin $A_{1b}$ may be obtained as described in U.S. Pat. No. 4,578,271 (WS-6049-A is esperamicin $A_{1b}$) or as described in J. Antibiotics 38 (11), 1605-1609, 1985. The producing microorganism disclosed in U.S. Pat. No. 4,578,271, i.e. ATCC 39100, has been deposited by applicant in the American Type Culture Collection (ATCC) under the accession number ATCC 53610.

The desired N-acetyl product may be isolated and purified by conventional chromatographic procedures such as exemplified in Example 1.

CHARACTERIZING DATA

The preferred product of the present invention, N-acetylesperamicin $A_1$, has been extensively characterized and demonstrates the following properties:

Physical description: amorphous pale yellow solid
Melting point: ~150° C. with decomposition
Elemental analysis:

| Analysis I | Analysis II |
|---|---|
| C = 54.36% | C = 54.80% |
| H = 5.59 | H = 6.07 |
| N = 4.15 | N = 4.19 |
| S = 9.69 | S = not analyzed |

Figure 1:
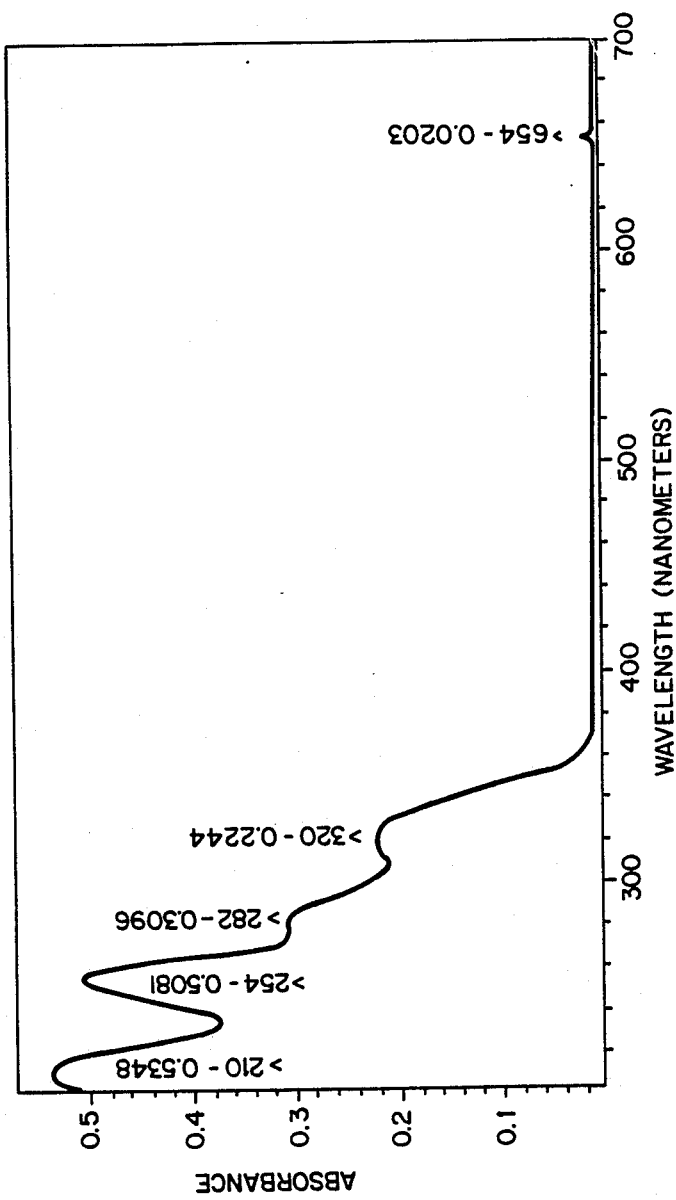
FIG. 1 shows the ultraviolet absorption spectrum of N-acetylesperamicin $A_1$ when dissolved in methanol at a concentration of 0.01848 g/l.

UV Spectrum: as shown in FIG. 1
solvent = methanol
concentration = 0.01848 g/l

| λmax (nm) | a | ε |
|---|---|---|
| 254 | 27.49 | 37,550 |
| 282 | 16.75 | 22,880 |
| 320 | 12.14 | 16,580 |

Figure 2:
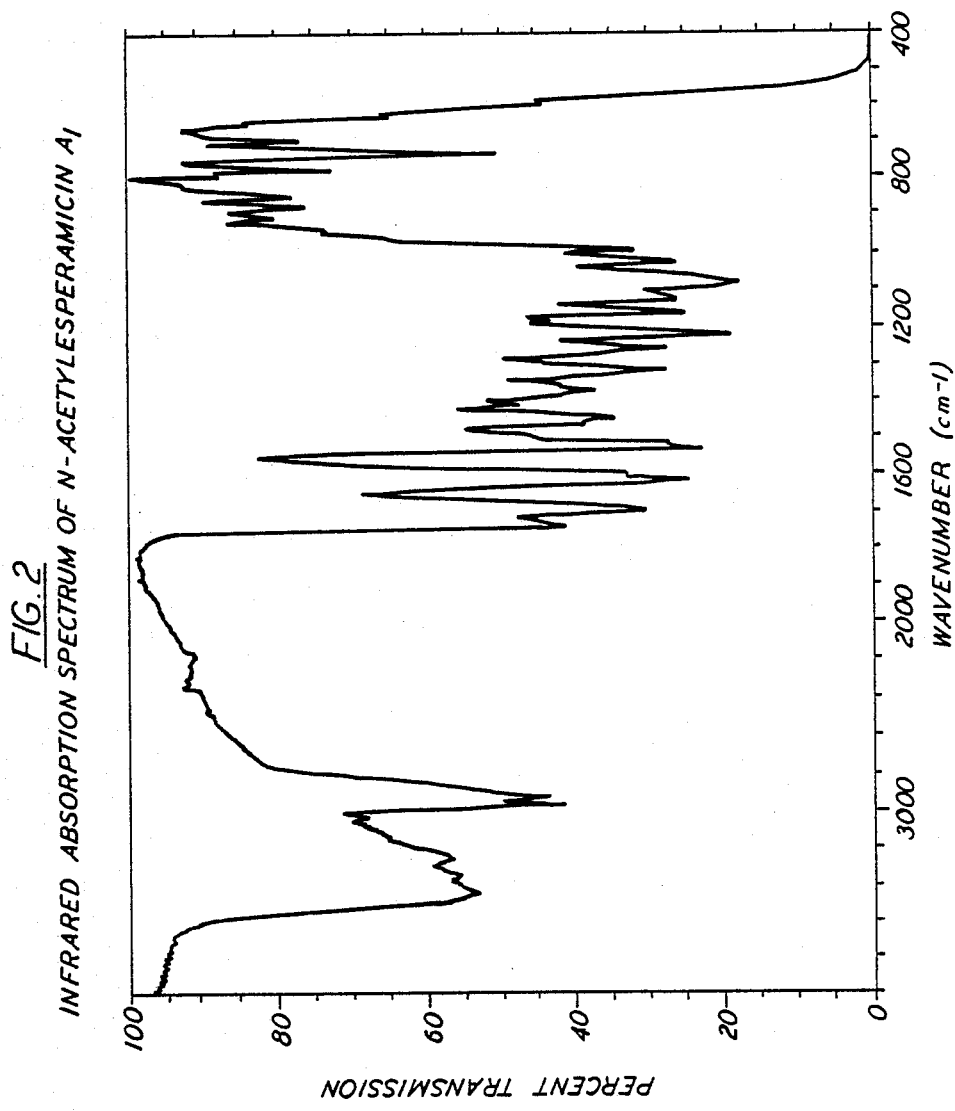
FIG. 2 shows the infrared absorption spectrum of N-acetylesperamicin $A_1$ (NaCl film).

IR Spectrum: as shown in FIG. 2
Phase = NaCl film
Major absorption bands:
3938, 3857, 3849, 3805, 3760, 3682, 3467, 3372, 3268, 3059, 2974, 2935, 2349, 2209, 1737, 1695, 1614, 1529, 1465, 1451, 1409, 1372, 1312, 1252, 1214, 1179, 1157, 1119, 1075, 1020, 990, 946, 915, 881, 854, 798, 780, 736, 703, 658, 632 $cm^{-1}$.

Figure 3:
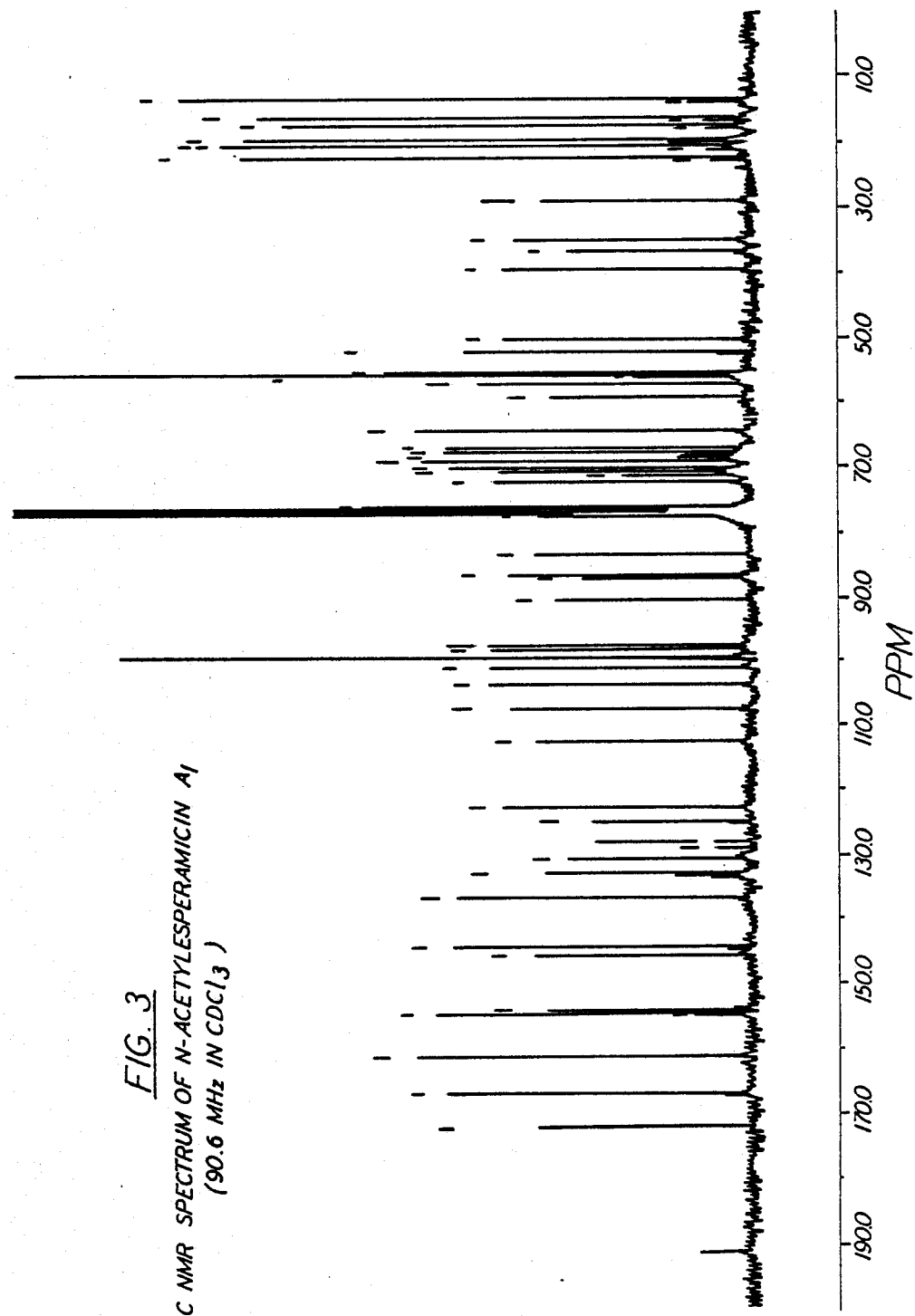
FIG. 3 shows the $^{13}C$ magnetic resonance spectrum of N-acetylesperamicin $A_1$ in $CDCl_3$ (90.55 MHz).

$^{13}C$ NMR Spectrum: as shown in FIG. 3
Instrument: Brucker WM-360 operated at 90.55 MHz; solvent = $CDCl_3$ δ (ppm): 13.7, 16.5, 17.6, 19.7, 20.6, 20.9, 22.6, 22.6, 28.9, 35.1, 36.6, 39.3, 50.2, 52.2, 55.5, 55.9, 55.9, 55.9, 57.0, 57.1, 59.4, 64.5, 67.0, 57.9, 68.5, 68.9, 69.6, 70.2, 70.8, 71.2, 72.1, 76.22, 77.3, 77.5, 83.2, 86.6, 90.4, 97.6, 97.7, 98.2, 99.5, 99.5, 101.1, 103.6, 107.5, 112.4, 122.7, 124.8, 130.6, 132.9, 133.0, 136.5, 143.9, 145.3, 153.7, 154.3, 154.7, 160.6, 166.6, 171.8, 191.0

Proton NMR Spectrum: as shown in FIG. 4

360.14 MHz = frequency $CD_3Cl$ = solvent

δ (ppm): 11.67 (1H, s), 8.88 (1H, brs), 8.44 (1H, s), 7.37 (1H, s), 6.62 (1H, dd, J=4.5, J=10.4), 6.20 (2H, s), 5.89 (1H, d, J=9.5), 5.76 (1H, d, J=9.4), 5.59 (1H, brs), 5.42-5.39 (3H), 4.92 (1H, d, J=10.0), 4.65-4.50 (5H), 4.06-3.54 [19H, 3.91 (3H, s), 3.81 (3H, s), 3.73 (3H, s)], 3.27 (3H, s), 3.25 (1H, m), 2.93 (1H, m), 2.80 (1H, brs), 2.60 (1H, m), 2.47 (3H, s), 2.46 (1H, m), 2.43 (4H, s), 2.11 (1H, obs), 2.10 (3H, s), 2.06 (3H, s), 1.48-1.36 (2H), 1.35 (3H, d, J=6.4), 1.29 (3H, d, J=6.4), 1.26 (3H, d, J=6), 1.20-1.12 (6H).

Mass Spectrum: Instrument: Kratos MS-50

Method: fast atom bombardment (FAB) ionization

Matrix: glycerol/LiCl

No molecular ions were observed. However the fragmentation pattern confirmed the proposed structure.

Based on the above properties, applicant has assigned structures for N-acetylesperamicins $A_1$, $A_2$ and $A_{1b}$ as indicated above.

BIOLOGICAL PROPERTIES

Antimicrobial activity of N-acetylesperamicin $A_1$ was determined for a variety of bacteria by the serial two-fold agar dilution method. Nutrient agar medium was used. As shown below the compound showed activity against a variety of pathogenic bacteria.

Antimicrobial Activity of N-Acetylesperamicin $A_1$

| Organism | MIC in mcg/ml |
| --- | --- |
| S. faecalis A20688 | .03 |
| S. faecalis/ATCC 29218 A25707 | .016 |
| S. faecalis/ATCC 33186 A15708 | .016 |
| S. aureus A9537 | .008 |
| S. aureus/NCCLS strain A20698 | .016 |
| S. aureus/ATCC 29213 A24407 | .03 |
| E. coli A15119 | 32 |
| E. coli/NCCLS strain A20697 | 8 |
| K. pneumoniae A9664 | 32 |
| K. pneumoniae A20468 | >125 |
| P. vulgaris A21559 | 125 |
| P. aeruginosa A9843 | >125 |
| P. aeruginosa/ATCC 23389 A20235 | 125 |
| P. aeruginosa/ATCC 27853 A21508 | >125 |
| B. subtilis/ATCC 6633 A9506-A | .03 |

N-Acetylesperamicin $A_1$ was also tested in the in vitro cytotoxicity assay. This assay involves growing various mammalian tumor cells, including human tumor cells, on microtiter plates employing established tissue culture methods. The concentration of compound required to inhibit cell growth by 50% ($IC_{50}$) was then determined by a four-fold serial dilution technique. The validity of the method has been supported by a report published in the "Proceedings of the American Association for Cancer Research", Vol. 25, 328, p. 1891 (1984). Tumor cells of the following types were employed: B16-F10 murine melanoma, Moser human colon, and three human colon tumor cell lines, namely HCT-116, HCT-VM34 and HCT/VP35, the latter two being resistant to teniposide (VM) and etoposide (VP).

CYTOTOXICITY ASSAY

| | $IC_{50}$ (mcg/ml) values* | | | | |
| --- | --- | --- | --- | --- | --- |
| Compound | B16-F10 | HCT-116 | HCT/VM34 | HCT/VP35 | Moser |
| N—acetyl-esperamicin $A_1$ | 0.0522 | 0.0135 | 0.30 | 0.0271 | 1.0 |

*values <500 mcg/ml are a positive indicator of activity

P388 In Vivo Murine Leukemia Assay

The test protocol involved $CDF_1$ female mice implanted intraperitoneally with a tumor inoculum of $10^6$ ascites cells of P388 murine leukemia and treated with various doses of test compound. The compound was administered by intraperitoneal injection on a certain dosage schedule, i.e. test drug given once on day one, the day of tumor inoculation. Groups of four mice were used for each dosage amount. A group of ten saline-treated control mice was employed.

The test compound was dissolved in a mixture of water and ethanol. Death or survival of the treated and non-treated mice was recorded daily, and the median survival time (MST) in days was calculated for the test (T) and control (C) groups. A T/C value equal to or greater than 125% indicates that a significant antitumor effect was achieved. Mice weighing 20 g each were employed and a loss in weight of up to about 2 grams was not considered excessive.

P388 In Vivo Antitumor Activity

| Compound | Dose (mg/kg) | MST (days) | % T/C | Average Wgt. change in g (day 4) | No. Mice alive on day 5/total |
| --- | --- | --- | --- | --- | --- |
| N—Acetyl-esperamicin $A_1$ | 0.0896 | TOX | TOX | −3.4 | 0/6 |
| | 0.0512 | 6.0 | 63 | −2.9 | 4/6 |
| | 0.0256 | 6.0 | 63 | −3.1 | 4/6 |
| | 0.0128 | 17.0 | 179 | −2.2 | 6/6 |
| | 0.0064 | 14.0 | 147 | −1.7 | 6/6 |
| | 0.0032 | 14.5 | 153 | −0.2 | 6/6 |
| | 0.0016 | 14.0 | 147 | −0.5 | 6/6 |
| Control (saline) | 0.5 ml | 9.5 | 100 | 1.1 | 10/10 |

As shown above the compounds of the present invention possess potent antibacterial activity and are thus useful in the therapeutic treatment of mammals and other animals for infectious diseases caused by such bacteria. Additionally they may be employed for other conventional applications of antimicrobial agents such as disinfecting medical and dental equipment.

The cytotoxicity data and in vivo murine tumor data shown above indicate that the compounds of the present invention are also therapeutically useful in inhibiting the growth of mammalian tumors.

The present invention, therefore, provides a method for therapeutically treating an animal host affected by a microbial infection or by a malignant tumor which comprises administering to said host an effective antimicrobial or tumor-inhibiting dose of N-acetylesperamicin $A_1$, $A_2$ or $A_{1b}$, or a pharmaceutical composition thereof.

In another aspect the present invention provides a pharmaceutical composition which comprises an effective antimicrobial or tumor-inhibiting amount of N-acetylesperamicin $A_1$, $A_2$ or $A_{1b}$ in combination with an inert pharmaceutically acceptable carrier or diluent. These compositions may be made up in any pharmaceutical form appropriate for parenteral administration.

Preparations according to the invention for parenteral administration include sterile aqueous or non-aqueous solutions, suspensions or emulsions. They may also be manufactured in the form of sterile solid compositions which can be dissolved in sterile water, physiological saline or some other sterile injectable medium immediately before use.

It will be appreciated that the actual preferred amounts of the N-acetyl derivatives used will vary according to the pparticular compound, the particular composition formulated, the mode of application and the particular situs, host and disease being treated. Many factors that modify the action of the drug will be taken into account by those skilled in the art, for example, age, body weight, sex, diet, time of administration, route of administration, rate of excretion, condition of the host, drug combinations, reaction sensitivities and severity of the disease. Administration can be carried out continuously or periodically within the maximum tolerated dose. Optimal application rates for a given set of conditions can be ascertained by those skilled in the art using conventional dosage determination tests in view of the above guidelines.

The following examples are provided for illustrative purposes only and are not intended to limit the scope of the invention.

EXAMPLE 1

N-Acetylesperamicin $A_1$

A sample of esperamicin $A_1$ (289 mg) was dissolved in 10 ml of dry methylene chloride and 1 ml of acetic anhydride was added. The reaction mixture was kept at room temperature under Argon in the dark for 48 hours. Progress of the reaction was monitored by thin layer chromatography (TLC). At the conclusion of the reaction the reaction solution was applied on a silica gel chromatography column (flash) $\phi 25$ cm $\times$ 10 cm (1) and washed with $CH_2Cl_2$ (200 ml) and then toluene-acetone (2:1 v/v). The eluant was monitored by TLC in the same solvent system ($R_f$ value for esperamicin $A_1$ was 0.15 and that for N-acetylesperamicin $A_1$ was 0.27). Appropriate fractions were pooled and evaporated to dryness to yield 217.1 mg of substantially pure N-acetylesperamicin $A_1$. Remaining fractions (2) after evaporation to dryness yielded 14.9 mg of a mixture of starting material (esperamicin $A_1$) and product in a 1:1 ratio and, in the last fraction, 32.3 mg of unreacted esperamicin $A_1$ starting material. These last-described two fractions were recycled under similar conditions as described above (24 hours, room temperature, 10 ml $CH_2Cl_2$/0.25 ml $Ac_2O$) to yield additional N-acetylesperamicin $A_1$. Separation by column chromatography and isolation yielded 25.1 mg of additional product. Overall yield = 84%.

EXAMPLE 2

N-Acetylesperamicin $A_1$

A sample of esperamicin $A_1$ (179.3 mg) was dissolved in dry $CH_2Cl_2$ and 0.5 ml of acetic anhydride was added. The reaction mixture was stirred overnight (16 hours) at 30° C. under Argon. (The slightly elevated temperature and stirring led to completion of the reaction after 16 hours, as opposed to the 48 hour reaction period in Example 1). Isolation of the product (only one product observed in this procedure) as in Example 1 gave 159.0 mg of pure N-acetylesperamicin $A_1$ (86% yield).

EXAMPLE 3

N-Acetylesperamicin $A_2$

Following the general procedure as described in Example 1 or Example 2 but with substitution of an equivalent weight of esperamicin $A_2$ for the esperamicin $A_1$ starting material used therein gives N-acetylesperamicin $A_2$.

EXAMPLE 4

N-Acetylesperamicin $A_{1b}$

Following the general procedure of Example 1 or 2 but with substitution of an equivalent weight of esperamicin $A_{1b}$ for the esperamicin $A_1$ starting material used therein gives N-acetylesperamicin $A_{1b}$.

We claim:

1. The compound N-acetylesperamicin $A_1$ having the formula

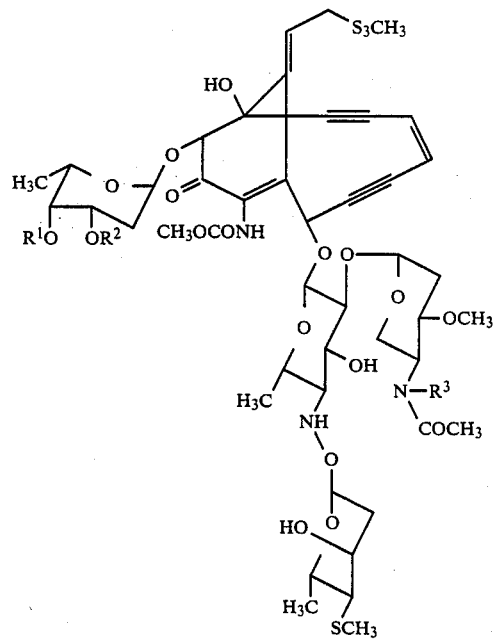

wherein $R^1$ is hydrogen, $R^2$ is

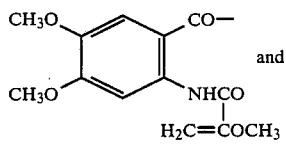

$R^3$ is —CH(CH$_3$)$_2$.

2. The compound N-acetylesperamicin A$_2$ having the formula

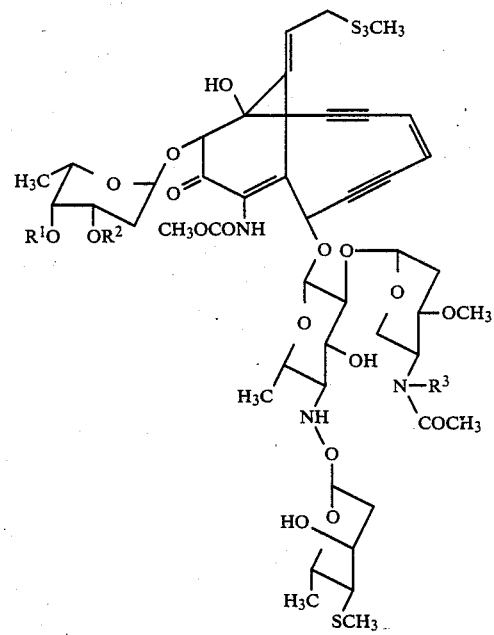

wherein R$^1$ is

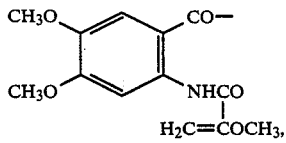

R$^2$ is hydrogen and R$^3$ is —CH(CH$_3$)$_2$.

3. The compound N-acetylesperamicin A$_{1b}$ having tthe formula

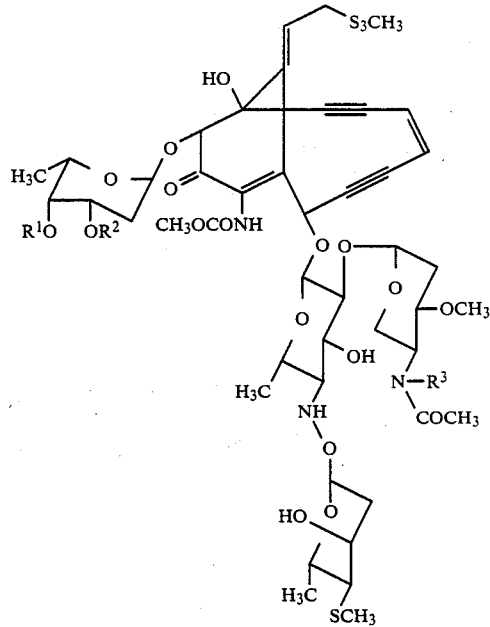

wherein R$^1$ is hydrogen, R$^2$ is

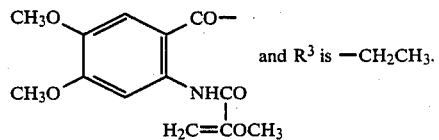

and R$^3$ is —CH$_2$CH$_3$.

4. A method for therapeutically treating an animal host affected by a microbial infection which comprises administering to said host an effective antimicrobial dose of N-acetylesperamicin A$_1$, N-acetylesperamicin A$_2$ or N-acetylesperamicin A$_{1b}$.

5. A pharmaceutical composition comprising an effective antimicrobial amount of N-acetylesperamicin A$_1$, N-acetylesperamicin A$_2$ or N-acetylesperamicin A$_{1b}$ in combination with a pharmaceutically acceptable carrier or diluent.

* * * * *